United States Patent
Kim et al.

(10) Patent No.: US 9,702,798 B1
(45) Date of Patent: Jul. 11, 2017

(54) METHOD FOR EVALUATING FRACTURE TOUGHNESS USING INSTRUMENTED INDENTATION TESTING

(71) Applicant: FRONTICS, INC, Seoul (KR)

(72) Inventors: Jun Yeong Kim, Seoul (KR); Dong Il Kwon, Seoul (KR); Kwang Ho Kim, Seongman-si (KR); Seung Won Jeon, Seoul (KR); Woo Joo Kim, Seoul (KR); Seung Hun Choi, Seoul (KR)

(73) Assignee: FRONTICS, INC. (KR)

( * ) Notice: Subject to any disclaimer, the term of this patent is extended or adjusted under 35 U.S.C. 154(b) by 0 days.

(21) Appl. No.: 15/269,012

(22) Filed: Sep. 19, 2016

(30) Foreign Application Priority Data

Jul. 27, 2016 (KR) .................. 10-2016-0095742

(51) Int. Cl.
  *G01N 3/00* (2006.01)
  *G01N 3/42* (2006.01)
  *G01N 3/08* (2006.01)

(52) U.S. Cl.
  CPC .............. *G01N 3/42* (2013.01); *G01N 3/08* (2013.01)

(58) Field of Classification Search
  CPC .................................. G01N 3/08; G01N 3/42
  USPC ........ 73/1.89, 81–83, 85–87, 783, 788, 799, 73/804, 821; 209/599
  See application file for complete search history.

(56) References Cited

U.S. PATENT DOCUMENTS

| | | | |
|---|---|---|---|
| 4,852,397 A * | 8/1989 | Haggag | G01N 3/42 73/82 |
| 6,718,820 B2 | 4/2004 | Kwon et al. | |
| 6,851,300 B2 | 2/2005 | Kwon et al. | |
| 7,472,603 B2 | 1/2009 | Kim | |
| 7,487,051 B2 | 2/2009 | Kim et al. | |
| 2010/0024534 A1 * | 2/2010 | Li et al. | G01N 3/42 73/81 |

FOREIGN PATENT DOCUMENTS

| KR | 2002-0076075 A | 10/2002 |
| KR | 100491295 B1 | 5/2005 |
| KR | 2008-0106746 A | 12/2008 |

OTHER PUBLICATIONS

Authors: Y. J . Xie, X. Z. Hu, J. Chen and K.Y. Lee, Title: Micro-indentation fracture from flat-ended cylindrical indenter, Date: 2011, Publication: Fatigue & Fracture of Engineering Materials & Structures, vol. 35, pp. 45-55.*

Author: unknown, Title: Instrumented Indentation Technique, Date: Apr. 2012, Publisher: Frontics, Inc., total pages: 15.*

Author: Hans-Jakob Schindler, Title: On quasi-non-destructive strength and toughness testing of elastic-plastic materials, Date: Aug. 25, 2004, Publisher: Science Direct, online at www.sciencedirect.com and Elsevier, International Journal of Solids and Structures 42 (2005) 717-725.*

(Continued)

*Primary Examiner* — Lisa Caputo
*Assistant Examiner* — Roger Hernandez-Prewitt
(74) *Attorney, Agent, or Firm* — Harness, Dickey & Pierce, P.L.C.

(57) ABSTRACT

The present invention relates to a method for measuring a fracture toughness using an instrumented indentation testing, which measures a load and an indentation depth in real time while applying a load to a specimen by an indenter having a flat punch shape.

8 Claims, 15 Drawing Sheets

(56) References Cited

OTHER PUBLICATIONS

Author: Y. J. Xie, X. Z. Hu, J. Chen and K.Y. Lee, Title: Micro-indentation fracture from flat-ended cylindrical indenter, Date: 2011, Publisher: Blackwell Publishing Ltd. Fatigue Fract Engng Mater Struct 35, 45-55.*

* cited by examiner

PRIOR ART

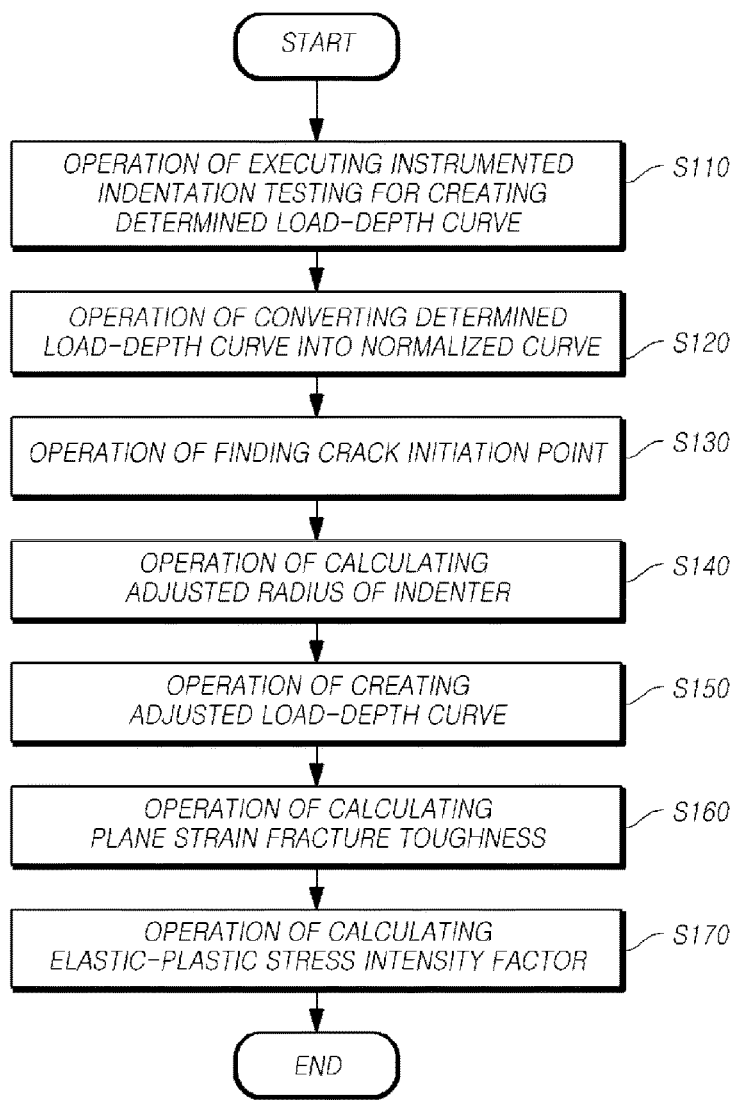

METHOD FOR EVALUATING FRACTURE TOUGHNESS USING INSTRUMENTED INDENTATION TESTING

CROSS REFERENCE TO RELATED APPLICATION

This application claims priority from Korean Patent Application No. 10-2016-0095742, filed on Jul. 27, 2016, which is hereby incorporated by reference for all purposes as if fully set forth herein.

BACKGROUND OF THE INVENTION

1. Field of the Invention

The present invention relates to a method for evaluating the fracture toughness using the instrumented indentation testing, and more particularly relates to a method for evaluating the fracture toughness by using the instrumented indentation testing, which enables direct measurement of physical properties in the field so that the structural integrity can be evaluated without separately collecting a specimen, which enables a calculation of the fracture toughness by executing the indentation testing through a theoretical and practical approach in order to thereby identify the resistance to the crack growth in the specimen, and which is useful enough to be used for the evaluation of the physical properties in the field, such as the evaluation of a change in the fracture toughness depending on the temperature or the evaluation of the structural integrity.

2. Description of the Prior Art

Since unexpected breakage of a large structure brings about significant losses, the evaluation of the structural integrity is performed in various manners in order to avoid the breakage. In order to evaluate the integrity of a structure that is in use, it is important to know exact information on the stress that is applied to the structure, information on the defects that exist inside the structure, and physical property information of a structure material. In particular, the breakage of the structure is caused by a change in the physical properties, such as a deterioration or embrittlement, in many cases, so it is required to measure the mechanical properties of a material that is in actual use, instead of the physical properties at the time when it is designed, to then be reflected. However, the conventional mechanical testing cannot be applied to evaluate, in real time, the mechanical properties of a structure that is in use because it is a destructive test in which the mechanical properties of a material are measured by making and breaking a standardized specimen.

The plane strain fracture toughness ($J_{IC}$) and the elastic-plastic stress intensity factor ($K_{JC}$), which show the fracture toughness that indicates the resistance to the crack growth of a material, are important dynamic parameters for evaluating the structural integrity. However, the fracture toughness measuring method according to the prior art requires a specimen of a specific shape and size in order to ensure the validity. That is, correct testing is established, in which a crack is formed in a specimen and the stress and strain around the crack are dynamically analysed in order to thereby measure the size and the growing direction of the crack, and thereafter, the conditions for the fracture may be obtained through the testing. The representative fracture toughness test methods include compact tension testing, which introduced fatigue precracking, and 3-point-single-edge notched bend testing. For the testing above, a plurality of specimens having a predetermined size are taken in a predetermined direction from the original plate (see ASTM specifications for the load direction and the crack growth direction), and the crack growth is recognized while actually breaking the same.

However, the complicated testing procedure including the fatigue precracking and the measurement of the crack length causes the fracture toughness measurement to be extremely difficult.

Furthermore, since the conventional fracture toughness measuring method is a destructive test in which a specimen is taken from the material to then be tested, it has limitations in being applied to industrial structures that are actually operated.

In the instrumented indentation testing that is proposed as an alternative to the same, the load and the indentation depth are measured in real time while applying a load to the surface of a specimen by using a sharp indenter, and then, a variety of mechanical properties of the material are evaluated through the analysis of a measured load-depth curve. Unlike the conventional testing methods, since this testing is a non-destructive mechanical test that leaves only a small indentation on the material surface, the physical properties can be directly measured on the spot, and a local property evaluation can be made through the testing in a local area. Therefore, the testing is widely used as micro/nanoscale mechanical testing, such as thin films or electronic components. Recently, a technique has been developed, which evaluates the tensile property, the residual stress, and the fracture toughness in the indentation testing, as well as the basic properties thereof, such as the hardness and the elastic modulus, based on dynamic modelling.

Among them, although the fracture toughness is the advanced physical property that is required for the destructive-dynamic analysis of the structural integrity, unlike the strength that is used in the general structural analysis, the analysis thereof is difficult because of the influences of various parameters (such as the crack length, the specimen shape, or the like) and the standardized fracture toughness testing is also difficult to be applied because of its complicated procedure and the nature of destructive testing. Thus, there have been many studies for evaluating or measuring the fracture toughness by using the indentation testing.

In addition, although it is considered that the confinement effect before the occurrence of the crack in the destructive testing is similar to the confinement effect that occurs under the indenter in the indentation testing in relation to the evaluating method of the fracture toughness by using the conventional indentation testing, in the strict sense, the destructive testing generates a plane-symmetrical stress field in the shape of a cylinder, whereas the indentation testing generates an axis-symmetrical stress field in the shape of a sphere. Accordingly, the fracture toughness may not be accurately evaluated by using the conventional indentation testing.

SUMMARY OF THE INVENTION

The present invention has been made from the background described above to provide a fracture toughness measuring method using the instrumented indentation testing, which enables direct measurement of the physical properties in the field so that the structural integrity can be evaluated without separately collecting a specimen, and which enables a calculation of the fracture toughness by executing the indentation testing through a theoretical and practical approach in order to thereby identify the resistance to the crack growth in the specimen.

In addition, the present invention provides a fracture toughness measuring method using the instrumented indentation testing, which is useful enough to be used for the evaluation of the physical properties in the field, such as the evaluation of a change in the fracture toughness depending on a temperature change or the evaluation of the structural integrity because the elastic-plastic stress intensity factor calculated according to the same matches the actually measured data within an error range of 20%.

The aspect of the present invention is not limited thereto, and other unmentioned aspects of the present invention may be clearly appreciated by those skilled in the art from the following descriptions.

According to the present invention, a method for measuring a fracture toughness using an instrumented indentation testing, which measures a load and an indentation depth in real time while applying a load to a specimen by an indenter having a flat punch shape, may include: executing an indentation testing up to a determined indentation depth by the indenter having a determined radius to create a determined load-depth curve; converting the determined load-depth curve into a normalized curve of a stress $$\left(\frac{L}{\pi a^2}\right)$$

and an indenter radius-to-indentation depth (h/a); finding a crack initiation point (P) by calculating the indenter radius-to-indentation depth and a crack initiation stress at a time point (P) at which a crack begins in the normalized curve; obtaining an adjusted radius of the indenter by calculating the crack initiation stress, the indenter radius-to-indentation depth at the crack initiation point (P), a configured radius of the indenter, or a configured indentation depth of the indenter; and creating an adjusted load-depth curve according to the indenter having the adjusted radius.

The present invention gives an effect of providing a fracture toughness measuring method using the instrumented indentation testing, which enables direct measurement of the physical properties in the field so that the structural integrity can be evaluated without separately collecting a specimen, and which enables a calculation of the fracture toughness by executing the indentation testing through a theoretical and practical approach in order to thereby identify the resistance to the crack growth in the specimen.

In addition, the present invention gives an effect of providing a fracture toughness measuring method using the instrumented indentation testing, which is useful enough to be used for the evaluation of the physical properties in the field, such as the evaluation of a change in the fracture toughness depending on a temperature change or the evaluation of the structural integrity because the elastic-plastic stress intensity factor calculated according to the same matches the actually measured data within an error range of 20%.

BRIEF DESCRIPTION OF THE DRAWINGS

The above and other objects, features, and advantages of the present invention will be more apparent from the following detailed description taken in conjunction with the accompanying drawings, in which:

FIG. 14 is a flowchart briefly illustrating a fracture toughness measuring method using the instrumented indentation testing and a process of calculating the plane strain fracture toughness and the elastic-plastic stress intensity factor, according to the present invention.

DETAILED DESCRIPTION OF THE EXEMPLARY EMBODIMENTS

Figure 1:
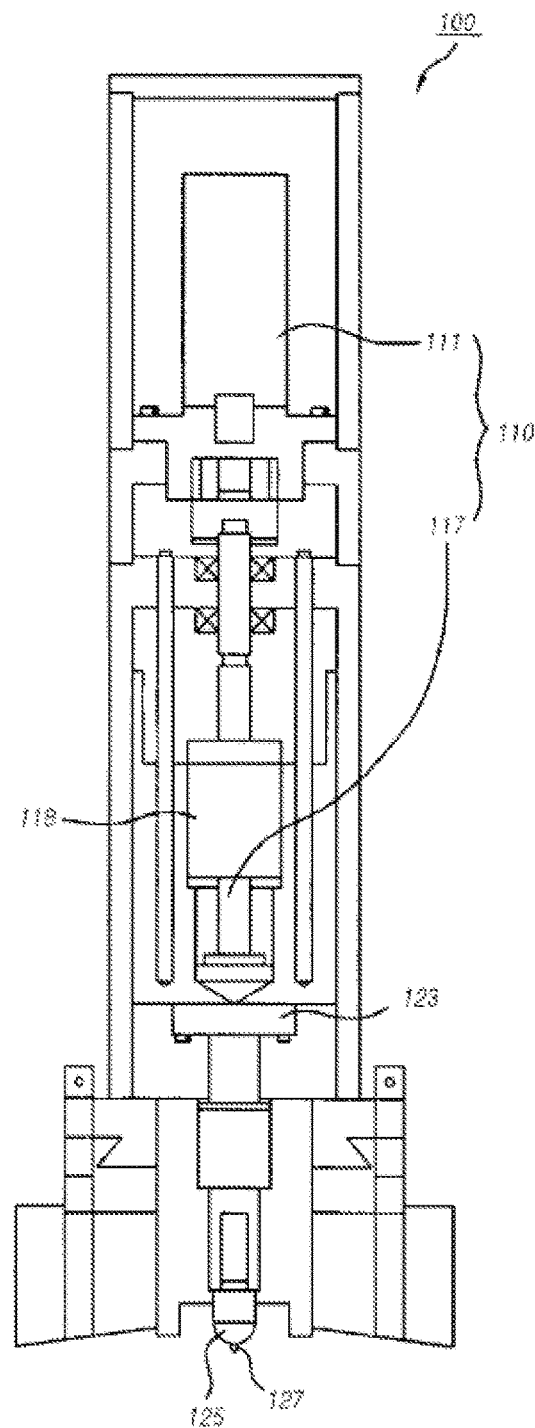
FIG. 1 is a cross-sectional view showing the structure of an indentation testing device that is used in the present invention.

Hereinafter, some embodiments of the present invention will be described in detail with reference to the accompanying drawings. In adding reference numerals to elements in each drawing, it should be noted that the same elements are designated by the same reference numerals, if possible, although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. These terms are merely used to distinguish one structural element from other structural elements, and a property, an order, a sequence and the like of a corresponding structural element are not limited by the term. It should be noted that if it is described in the specification that one component is "connected," "coupled" or "joined" to another component, a third component may be "connected," "coupled," and "joined" between the first and second components, although the first component may be directly connected, coupled or joined to the second component.

Figure 2:
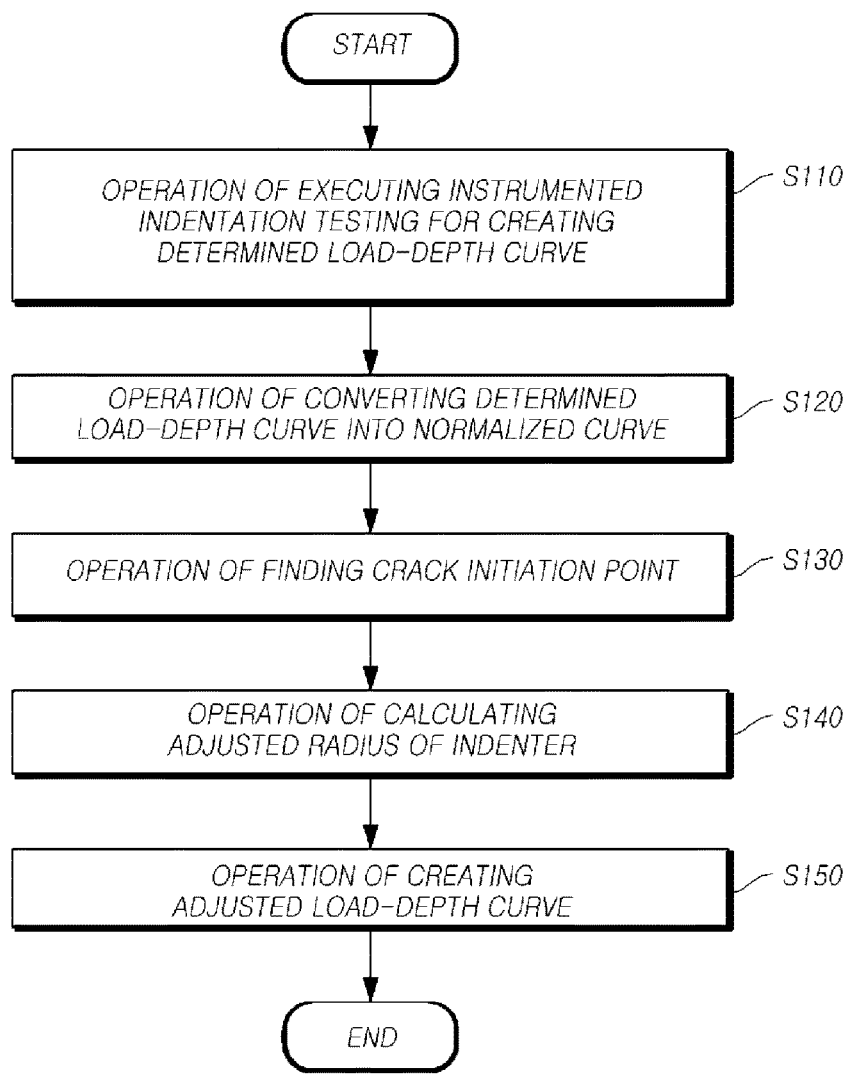
FIG. 2 is a flowchart briefly illustrating a fracture toughness measuring method using the instrumented indentation testing, according to the present invention.
Figure 3:
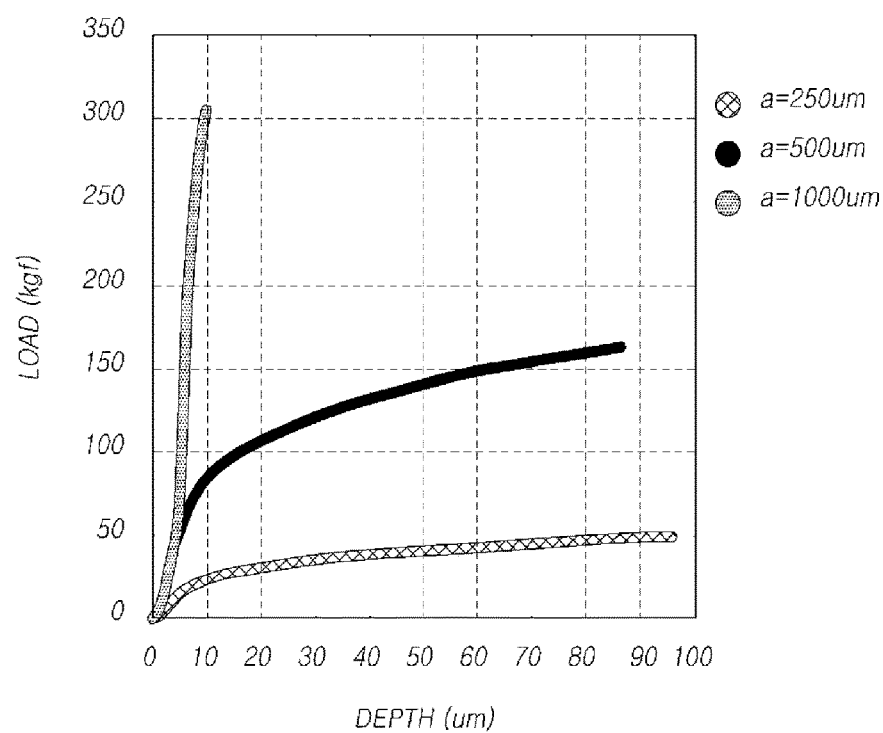
FIG. 3 shows a load-depth curve that is created by using indenters having various sizes.
Figure 4:
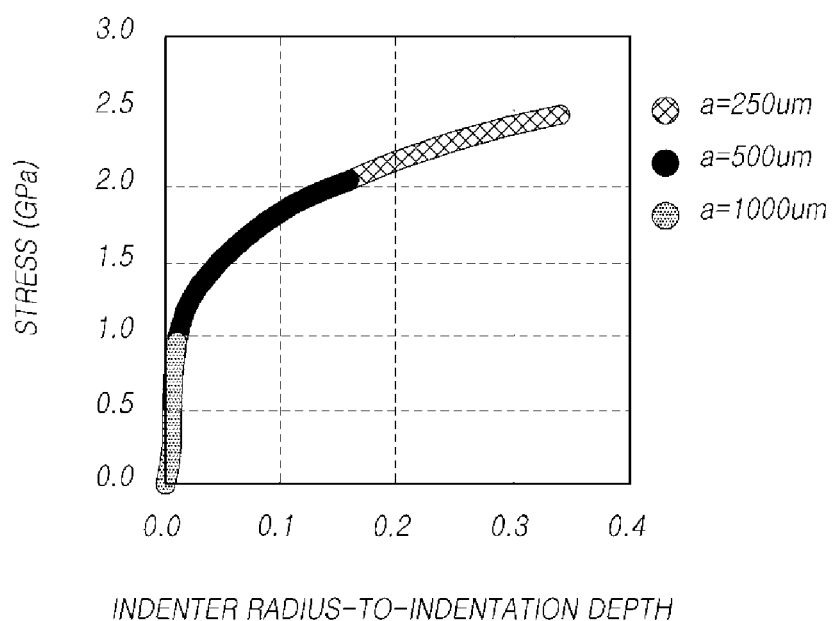
FIG. 4 is a diagram showing a normalized curve of the stress and the indenter radius to the indentation depth, which is converted from the load-depth curve of FIG. 3.
Figure 5:
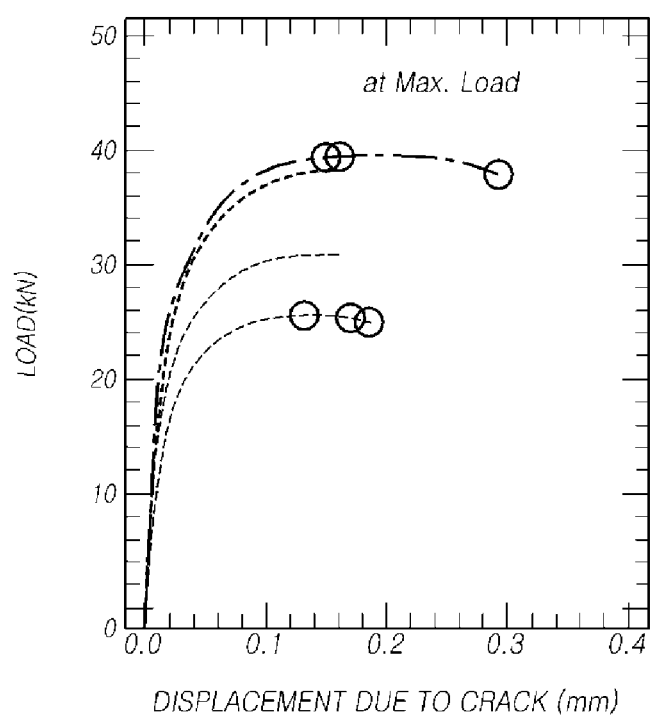
FIG. 5 is a diagram showing the load depending on the crack growth in a cracked round bar specimen of a ductile material according to the fracture testing.
Figure 6:
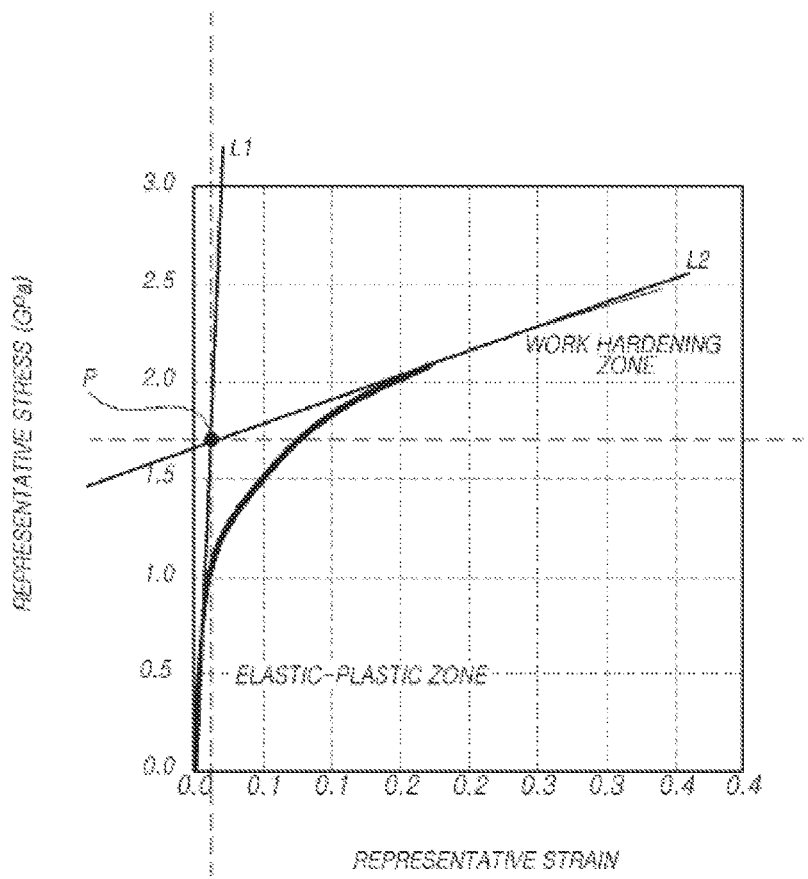
FIGS. 6 and 7 are diagrams showing a process of finding a crack initiation point in the normalized curve in the case of a ductile fracture model.
Figure 7:
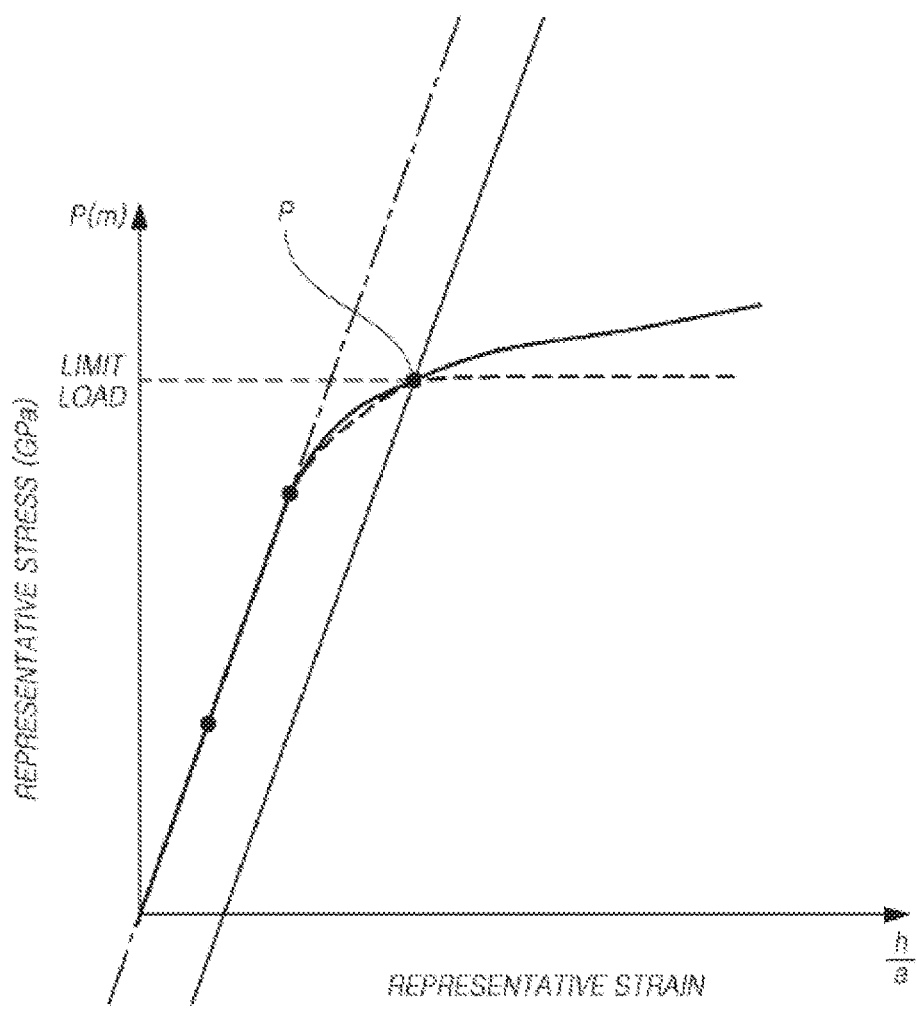
Figure 8:
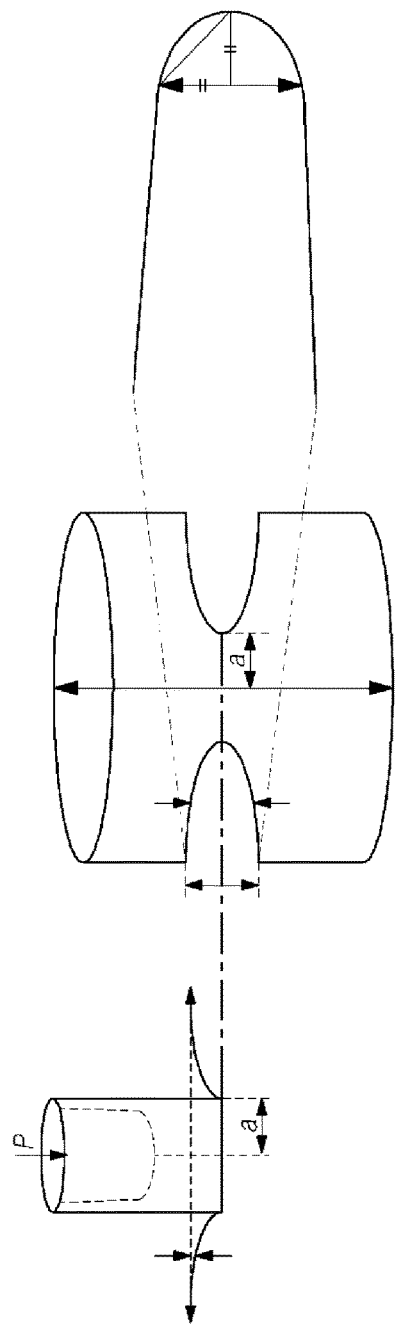
FIG. 8 illustrates a cracked round bar specimen in more detail.
Figure 9:
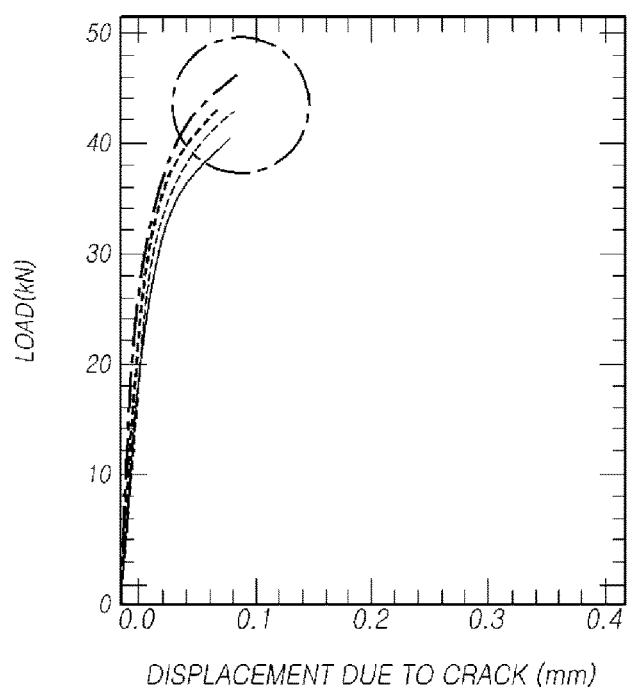
FIG. 9 is a diagram showing the load depending on the crack growth of a cracked round bar specimen of a brittle material according to the destructive testing.
Figure 10:
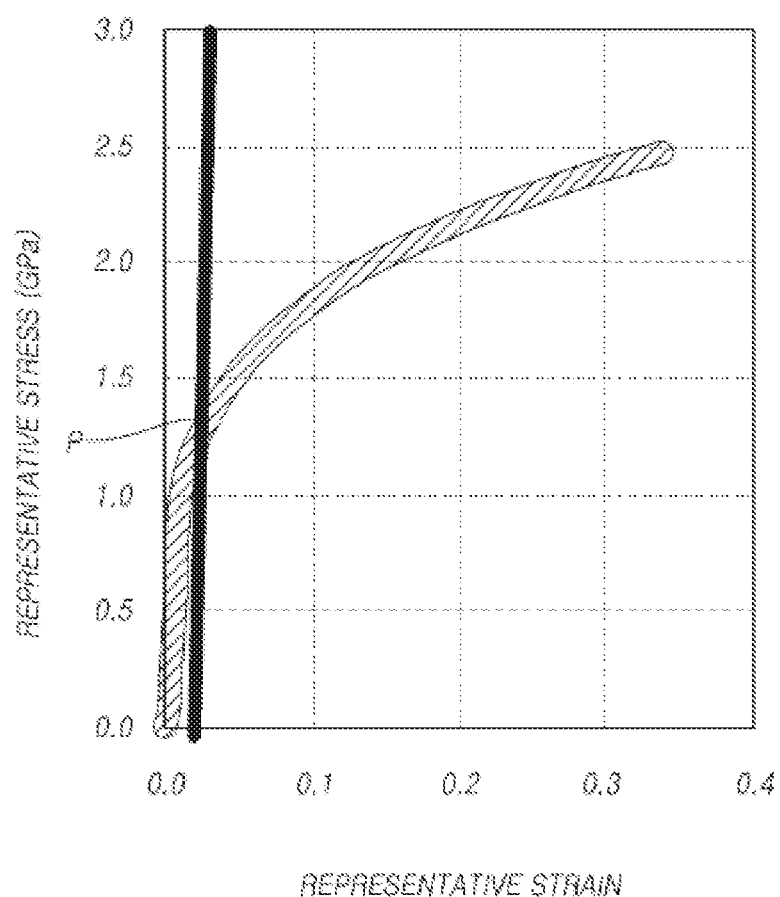
FIG. 10 is a diagram showing a process of finding a crack initiation point in the normalized curve in the case of a brittle fracture model.
Figure 11A:
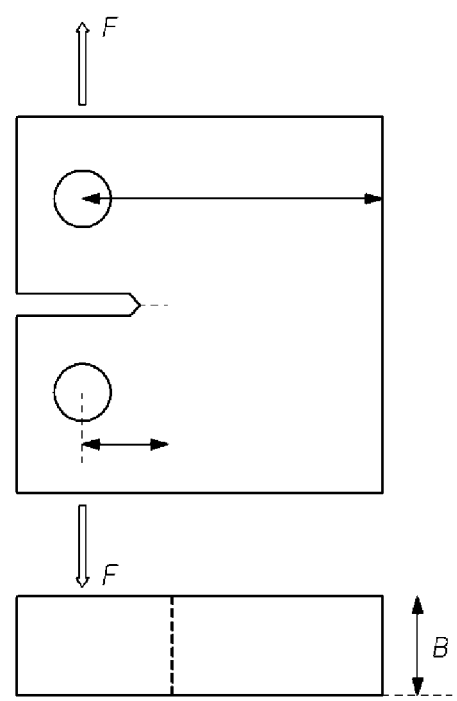
FIG. 11A is a view showing a standard specimen.
Figure 11B:
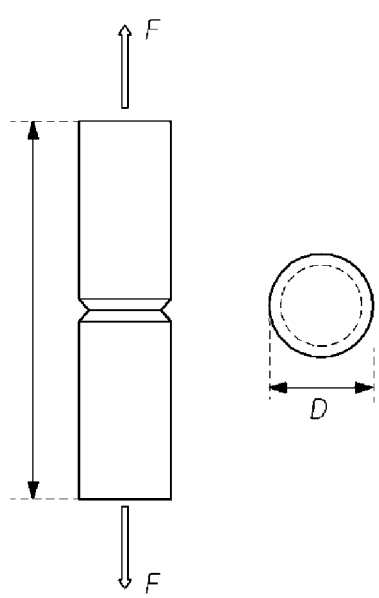
FIG. 11B is a view showing a cracked round bar specimen.
Figure 12:
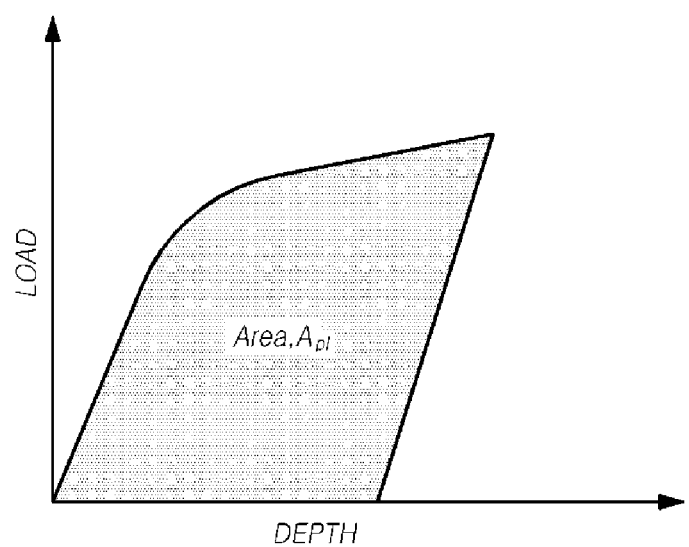
FIG. 12 is a view showing the area of the adjusted load-depth curve with respect to the x-axis to the crack initiation point.
Figure 13:
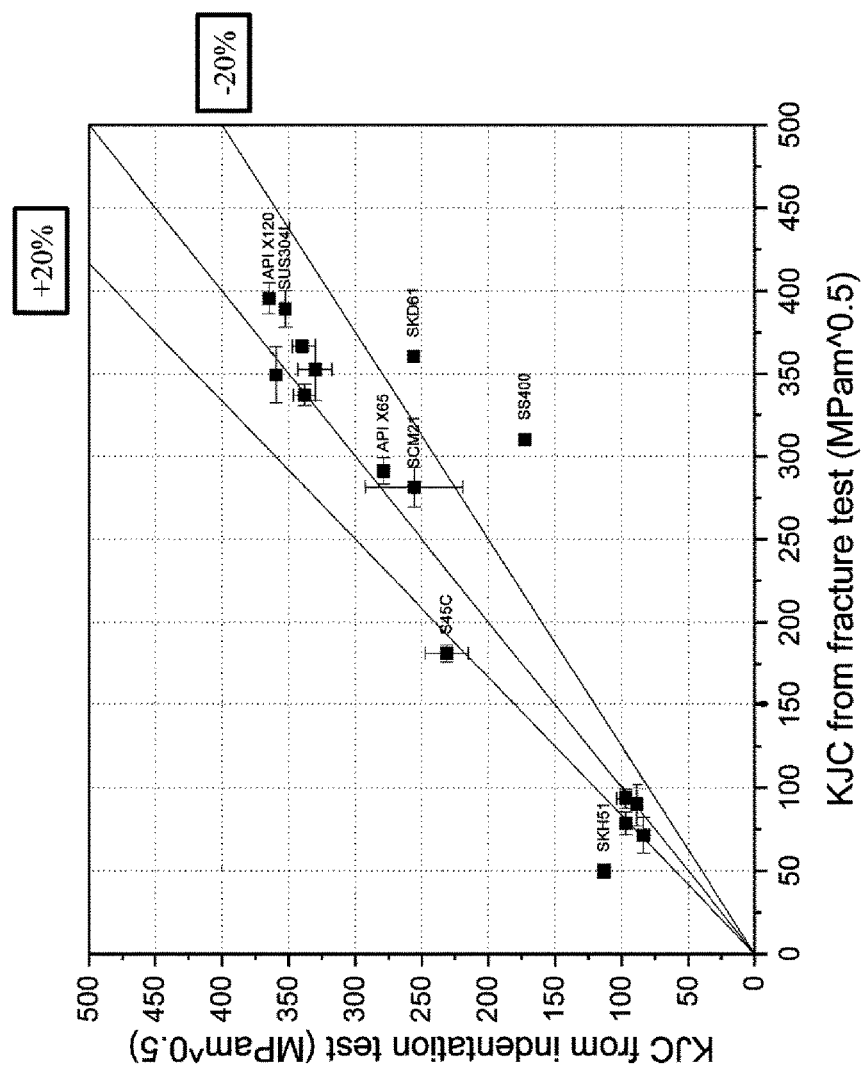
FIG. 13 is a graph that compares the elastic-plastic stress intensity factor actually obtained by the standard testing with the elastic-plastic stress intensity factor obtained according to the present invention.

FIG. 1 is a cross-sectional view showing the structure of an indentation testing device that is used in the present invention, and FIG. 2 is a flowchart briefly illustrating a fracture toughness measuring method using the instrumented indentation testing, according to the present invention. FIG. 3 shows a load-depth curve that is created by using indenters having various sizes, and FIG. 4 is a diagram showing a normalized curve of the stress and the indenter radius to the indentation depth, which is converted from the load-depth curve of FIG. 3. FIG. 5 is a diagram showing the load depending on the crack growth in a cracked round bar specimen of a ductile material according to the fracture testing, and FIGS. 6 and 7 are diagrams showing a process of finding a crack initiation point in the normalized curve in the case of a ductile fracture model. FIG. 8 illustrates a cracked round bar specimen in more detail, and FIG. 9 is a diagram showing the load depending on the crack growth of a cracked round bar specimen of a brittle material according to the destructive test. FIG. 10 is a diagram showing a process of finding a crack initiation point in the normalized curve in the case of a brittle fracture model, and FIG. 11A is a view showing a standard specimen and FIG. 11B is a view showing a cracked round bar specimen. FIG. 12 is a view showing the area of the adjusted load-depth curve with respect to the x-axis to the crack initiation point, and FIG. 13 is a graph that compares the elastic-plastic stress intensity factor actually obtained by standard testing with the elastic-plastic stress intensity factor obtained according to the present invention. FIG. 14 is a flowchart briefly illustrating a fracture toughness measuring method using the instrumented indentation testing and a process of calculating the plane strain fracture toughness and the elastic-plastic stress intensity factor, according to the present invention.

Referring to FIG. 1, in the present invention, the physical properties of a material may be measured by an indentation testing device 100 that is disclosed in U.S. Pat. No. 7,487,051 (Indentation testing device, indentation testing data measuring method and physical property measuring method using indentation testing device, and recording medium storing physical property measuring method).

The indentation testing device 100 may include a load applying device 110 that generates a load (L) through the rotation of a motor 111, a load sensor 123, an indenter holder 125, an indenter 127, and the like.

The rotational force that is generated from the motor 111 may rotate a ball screw 117 in order to thereby allow a ball screw nut 118 to reciprocate up and down.

At this time, the vertical pressure is transferred to the specimen through the indenter 127 in order to thereby generate a compression stress. When the motor 111 begins to rotate to apply a load (L) to the specimen, the load sensor 123 continuously measures a change in the load (L) that is applied to the specimen. In addition, a displacement sensor that is provided in the indentation testing device 100 continuously measures the indentation depth (h) of the indenter 127.

The load (L) and the indentation depth (h) are measured in real time up to a certain depth by the load sensor 123 and the displacement sensor in order to thereby complete a load-depth curve.

The present invention uses a method for measuring the physical properties of a material while applying a load (L) to the material through the instrumented indentation testing by using the indentation testing device 100, which is the same as the prior art described above, so the detailed description thereof will be omitted to avoid duplication.

In addition, the fracture toughness measuring method using the instrumented indentation testing disclosed in the present invention is applicable to various materials, such as a polymer, as well as to a metal material, for the measurement of the fracture toughness, and in the present invention, the description will be made of a fracture toughness measuring method using the instrumented indentation testing with respect to a metal material for the convenience of explanation.

The fracture toughness measuring method using the instrumented indentation testing, according to the embodiments, will be described with reference to FIGS. 2 to 14.

The present invention obtains the fracture toughness by developing a fracture toughness measuring model of a specimen by using the indentation testing through a theoretical and practical approach without destruction or damage of the specimen.

In order to directly associate the indentation behaviour of the specimen according to the indentation testing with the cracking behaviour of the specimen according to the fracture testing, and in order to match the stress state under the indenter that applies the load (L) in the indentation testing with the stress state before the crack tip in the fracture testing of the specimen, an indenter in a flat punch shape, which has a flat contact portion, is used instead of the conventional spherical indenter that has been widely used.

The indenter in a flat punch shape imitates a cracked round bar specimen, and is inspired by the fact that the pressing of the indenter in a flat punch shape onto the specimen is similar to the shape in which the cracked round bar with a crack in the circumferential direction is pulled. According to this, a load-depth curve is created through the instrumented indentation testing and the fracture toughness is calculated from the load-depth curve.

In particular, the load-depth curve may be created by using the instrumented indentation testing for measuring the load (L) and the indentation depth (h) in real time while applying the load (L) to the specimen with the indenter in a flat punch shape, and the fracture toughness may be calculated by using the same.

According to this, the indentation behaviour of the specimen is directly associated with the cracking behaviour of the specimen in order to thereby perform the modelling in a manner of inducing the virtual fracture toughness beyond the simple energy correlation, which will be described in more detail below.

First, since the indentation testing does not generate a crack, the conditions for determining the crack initiation point (P) of the fracture testing in the indentation situation are configured in a theoretical/engineering point of view.

At this time, in the present invention, a condition for the specimen size of the fracture toughness, which has not been considered in the previous studies, is applied to the indentation situation in order to thereby conform to the standard test conditions.

In addition, a ductile fracture model and a brittle fracture model are separated according to the general fracture behaviour of a specimen in order to thereby calculate the crack initiation point (P) and the size of the indenter in different manners.

After calculating the crack initiation point (P) and the size of the indenter, an adjusted load-depth curve is obtained, and in order to evaluate the structural integrity, the plane strain fracture toughness ($J_{IC}$) and the elastic-plastic stress intensity factor ($K_{JC}$) are calculated, which show the fracture toughness that indicates the resistance to the crack growth of a material.

According to this, referring to FIG. 2, which is a flowchart briefly illustrating a fracture toughness measuring method using the instrumented indentation testing, a fracture toughness measuring method using the instrumented indentation testing may include: operation S110 of executing the indentation testing up to a determined indentation depth (h) by using an indenter having a determined radius (a) in order to thereby create a determined load-depth curve; operation S120 of converting the determined load-depth curve into a normalized curve of the stress $$\left(\frac{L}{\pi a^2}\right)$$

and the indenter radius to the indentation depth (h/a); operation S130 of finding a crack initiation point (P by obtaining the crack initiation stress and the indenter radius-to-indentation depth at the crack initiation point (P in the normalized curve; operation S140 of obtaining an adjusted radius (a') of the indenter by calculating the crack initiation stress, the indenter radius-to-indentation depth at the crack initiation point (P), a configured radius of the indenter, or a configured indentation depth (h) of the indenter; and operation S150 of creating an adjusted load-depth curve according to the indenter that has the adjusted radius (a').

In operation S110 of executing the indentation testing for creating the determined load-depth curve, the indentation testing is executed up to a certain determined indentation depth (h) by using an indenter having a certain determined radius (a) by using the instrumented indentation testing.

As shown in FIG. 3 showing the load-depth curve that is created by executing the indentation testing by using indenters in a flat punch shape, which have various radiuses, the larger the radius of the indenter is, the smaller the indentation depth (h) for the same load (L) is. Thus, the load-depth curve varies depending on the radius of the indenter.

At this time, the determined load-depth curve, which is created in the indentation testing execution operation S110, shows the load (L) depending on the indentation depth (h) {the y-axis denotes the load (L) and the x-axis denotes the indentation depth (h), and the unit of the load (L) is kgf and the unit of the indentation depth (h) is μm}.

That is, the larger the radius (a) of the indenter is, the larger the contact area ($\pi a^2$) with the specimen is. In addition, as the radius (a) of the indenter increases, the load (L) increases, even with a small indentation depth (h).

In addition, since the load (L) depending on the indentation depth (h) varies with the radius (a) of the indenter, operation S120 of converting the determined load-depth curve into a normalized curve of the stress $$\left(\frac{L}{\pi a^2}\right)$$

and the indenter radius to the indentation depth (h/a) is executed in order to identify a graph of the load (L) depending on the indentation depth (h) regardless of the radius (a) of the indenter.

In order to convert the determined load-depth curve into the normalized curve of the stress $$\left(\frac{L}{\pi a^2}\right)$$

and the indenter radius to the indentation depth (h/a), the load (L) is divided by the contact area ($\pi a^2$) between the indenter and the specimen, and the indentation depth (h) is divided by the radius (a) of the indenter.

A value obtained by dividing the load (L) by the contact area ($\pi a^2$) between the indenter and the specimen is regarded as the stress $$\left(\frac{L}{\pi a^2}\right),$$

and a value obtained by dividing the indentation depth (h) by the radius (a) of the indenter is regarded as the indenter radius to the indentation depth (h/a).

FIG. 4 is a diagram showing the normalized curve that is converted from the load-depth curve by using the indenters in a flat punch shape, which have various indenter radiuses (a).

As shown in FIG. 4, the normalized curve shows the stress $$\left(\frac{L}{\pi a^2}\right)$$

depending on the indenter radius to the indentation depth (h/a), wherein the y-axis denotes thestress $$\left(\frac{L}{\pi a^2}\right)$$

and the x-axis denotes the indenter radius to the indentation depth (h/a). The normalized curve is used to evaluate the crack initiation point (P) and the tensile properties of the specimen, wherein the unit of the stress $$\left(\frac{L}{\pi a^2}\right)$$

is GPa and the indenter radius to the indentation depth (h/a) has a dimensionless number.

In addition, the same normalized curve may be obtained by converting the load-depth curve that is created through the indentation testing by using another indenter size. Thus, on the contrary, if the indenter size is determined, the load-depth curve according to the indenter size may be created by converting the normalized curve.

By using the normalized curve, operation S130 of finding the crack initiation point (P) is executed by obtaining the crack initiation stress and the indenter radius to the indentation depth (h/a) at the crack initiation point (P), and then, operation S140 of obtaining the adjusted radius (a') of the indenter is executed by calculating the obtained crack initiation stress, the indenter radius-to-indentation depth at the crack initiation point (P), a configured radius of the indenter, or a configured indentation depth (h) of the indenter.

Operation S130 of finding the crack initiation point (P) and operation S140 of calculating the adjusted radius (a') of the indenter may be executed separately according to a ductile fracture model and a brittle fracture model through the general fracture behaviour of the specimen.

First, FIGS. 5 to 8 show the ductile fracture model of a specimen. Here, FIG. 5 is a diagram showing the load depending on the crack growth in a cracked round bar specimen according to the fracture testing, and FIGS. 6 and 7 are diagrams showing a process of finding a crack initiation point (P) in the normalized curve. In addition, FIG. 8 shows that the crack growth of the cracked round bar specimen is the indentation depth (h) in the indentation testing.

FIG. 5 is a view showing the crack growth depending on the load as a result of testing the specimen of the ductile fracture model in the actual fracture toughness testing, wherein the x-axis denotes a displacement (the unit is mm) caused by the crack and the y-axis denotes the load (the unit is kN) applied to the specimen.

The crack initiation point (P) is measured by a point at which the maximum load occurs in the drawing showing the crack growth depending on the load in the fracture toughness testing described above. Similarly, in the present invention, the crack initiation point (P may be measured by calculating the maximum load in the load-depth curve of the indentation testing.

That is, in the case of a specimen of the ductile fracture model, the crack initiation point (P) in the actual fracture testing may be measured by using the maximum load that is one of the dynamic parameters, and the crack initiation point (P) is measured by calculating the maximum load in the indentation testing.

Alternatively, the load-depth curve obtained in the indentation testing is converted into the normalized curve, and then, the crack initiation point (P) is measured by calculating the intersection of the tangential line of the initial linear behaviour and the tangential line of the strain hardening behaviour in the normalized curve.

In this regard, as shown in FIG. 6, the first method of measuring the crack initiation point may include: executing the indentation testing up to the determined indentation depth (h) by using an indenter having a determined radius (a) in order to thereby create a determined load-depth curve; and regarding, as the crack initiation point, the intersection of the first line (L1) that extends from the elastic-plastic zone and the second line (L2) that extends from the strain hardening zone in the normalized curve that is converted from the determined load-depth curve.

FIG. 6 shows the first line (L1) that extends from the elastic-plastic zone and the second line (L2) that extends from the strain hardening zone in the normalized curve, and further shows the crack initiation point that is the intersection of the first line (L1) and the second line (L2).

In the concept of the maximum load, since no strain hardening occurs in the ideal perfect plastic body, the crack is considered to be generated at the intersection of the extension line of the elastic-plastic zone and the extension line of the strain hardening zone, and the intersection is regarded as the crack initiation point (P).

The stress $$\left(\frac{L}{\pi a^2}\right)$$

and the indenter radius to the indentation depth (h/a) at the intersection of the extension line of the elastic-plastic zone and the extension line of the strain hardening zone refer to the crack initiation stress and the indenter radius-to-indentation depth at the crack initiation point (P), respectively, and the adjusted radius (a') for executing the indentation testing corresponding to the actual fracture testing may be calculated.

In addition, in the second method of measuring the crack initiation point (P), as shown in FIG. 7, the crack initiation point (P) may be measured by using the maximum load of the normalized curve, and the maximum load may be obtained by an offset method in which the intersection is taken by offsetting the line of the elastic deformation zone by 0.2% in the normalized curve.

In the offset method in the case of a metal material, a line is drawn in parallel with the line of the elastic deformation zone to the point in which the strain is 0.2% in order to thereby obtain the yield strength (that is, the maximum load in the present invention) through the intersection of the parallel line and the normalized curve.

In addition, the crack initiation stress may be obtained by multiplying the stress $$\left(\frac{L}{\pi a^2}\right)$$

of the obtained yield strength by 3.285. Here, since the radius (a) of the indenter is extremely small compared to the specimen according to the Von Mises yield criterion, the indentation load (L) at the crack initiation point may be obtained by multiplying the stress $$\left(\frac{L}{\pi a^2}\right)$$

of the yield strength by 3.285 and the contact area ($\pi a^2$) of the indenter.

After the crack initiation point (P) is determined as described above, the indentation depth (h) is configured. As shown in FIG. 8, the pressing of the indenter having a radius (a) onto the specimen results in the same geometric similarity as a blunt crack of the cracked round bar specimen having a radius (a) of the minimum circumference. The blunt crack has a shape of an isosceles triangle when it is magnified. Thus, when the blunt crack grows by 0.2 mm, the indentation depth is also considered to increase by 0.2 mm.

In other words, the indentation depth (h) is regarded as the virtual crack growth based on the geometric similarity of the indenter in a flat punch shape and the fracture specimen in a cylindrical shape in order to thereby configure the indentation depth (h) corresponding to the crack growth of 0.2 mm as the engineering standard so that the size of the indenter corresponding to the specimen size condition of the fracture toughness may be determined.

That is, the indentation depth (h) is regarded as the virtual crack growth based on the geometric similarity of the indenter in a flat punch shape and the fracture specimen in a cylindrical shape in order to thereby configure the indentation depth (h) corresponding to the crack growth of 0.2 mm so that the size of the indenter corresponding to the specimen size condition of the fracture toughness may be determined.

According to this, the x-coordinate value of the crack initiation point refers to the indenter radius to the indentation depth (h/a) at the crack initiation point (P), and since that is a point in which the crack is initiated when the indentation depth (h) is 0.2 mm, the adjusted radius (a') may be obtained by dividing 0.2 mm by the indenter radius to the indentation depth (h/a) at the crack initiation point (P).

In addition, the indentation load (L) at the crack initiation point (P) may be obtained by multiplying the crack initiation stress by the contact area ($\pi a'^2$) of the indenter, which is formed by means of the adjusted radius (a').

Meanwhile, FIGS. 9 to 11 show a specimen of the brittle fracture model. FIG. 9 is a diagram showing the load depending on the crack growth of a cracked round bar specimen according to the destructive test, and FIG. 10 is a diagram showing a process of finding a crack initiation point in the normalized curve. In addition, FIG. 11A is a view showing a standard specimen, and FIG. 11B is a view showing a cracked round bar specimen.

FIG. 9 is a view showing the crack growth depending on the load as a result of testing the specimen of the brittle fracture model in the actual fracture toughness testing, wherein the x-axis denotes a displacement (the unit is mm) caused by the crack and the y-axis denotes the load (the unit is kN) applied to the specimen.

The crack initiation point (P) is measured by a start point of the non-linear behaviour in the drawing showing the crack growth depending on the load in the fracture toughness testing described above. Similarly, in the present invention, the crack initiation point (P) may be measured by calculating the maximum load in which the elastic deformation zone ends in the load-depth curve of the indentation testing.

In the case of the brittle fracture model, the crack initiation point (P) is regarded as a point at which the initial linearity ends in the load-depth curve based on the engineering approach, and the crack initiation point (P) may be measured by using a 95%-line-dividing technique.

Alternatively, the crack initiation point (P) may be measured by using the 0.2%-offset-technique that is used to determine the start point of the non-linear behaviour in the load-depth curve or in the normalized curve.

In this regard, as shown in FIG. 10, the method for measuring the crack initiation point may include: finding the maximum load by using the offset method in the normalized curve; horizontally shifting a line in the elastic deformation zone of the normalized curve by 0.2% by applying the 0.2%-offset method corresponding to a metal; and finding the intersection of the line and the normalized curve in order to thereby obtain the yield strength (the maximum load).

The obtained yield strength is measured as the crack initiation point (P), wherein the x-coordinate value of the yield strength denotes the indenter radius-to-indentation depth at the crack initiation point and the y-coordinate value of the yield strength denotes the crack initiation stress, respectively.

In addition, as shown in FIG. 11A, the portion in which the crack occurs in the standard specimen corresponds to the thickness of the standard specimen.

In addition, as shown in FIG. 11B, the portion in which the crack occurs in the cracked round bar specimen corresponds to the circumference of a circle, and the boundary to be applied with the load (L) also corresponds to the circumference of a circle.

At this time, unlike the ductile fracture model, in the case of the brittle fracture model, the fracture toughness varies with the size of the specimen in the fracture toughness testing. Therefore, according to a method for converting the specimen into a specimen having a thickness of 1 inch in order to thereby evaluate the fracture toughness, a specimen is configured to have a thickness of 1 inch to correspond to the actual fracture toughness result in the present invention.

Accordingly, the thickness of the standard specimen may be the circumference of the portion in which the crack occurs in the cracked round bar specimen, and may be the circumference of the indenter in the indentation testing.

Therefore, the radius (a') of the indenter having a circumference of 1 inch (=25.4 mm) may be 4.042 mm that is obtained by dividing 25.4 mm by $2\pi$. That is, the adjusted radius (a') of the indenter is 4.042 mm.

In addition, the indentation load (L) at the crack initiation point (P) is obtained by multiplying the crack initiation stress by the contact area ($\pi a'^2$) of the indenter, which is formed by means of the adjusted radius (a').

After executing operation S130 of finding the crack initiation point (P) and operation S140 of calculating the adjusted radius (a') of the indenter, operation S150 of creating an adjusted load-depth curve by the indenter having the adjusted radius (a') is executed.

The adjusted load-depth curve may be converted by multiplying the stress $$\left(\frac{L}{\pi a^2}\right)$$

and the indenter radius to the indentation depth (h/a) of the normalized curve by the contact area ($\pi a'^2$) of the indenter having the adjusted radius (a') and the adjusted radius (a') of the indenter.

Alternatively, the adjusted load-depth curve may be created by executing the instrumented indentation testing once more, which measures the load (L) and the indentation depth (h) while applying the load to the specimen by using the indenter having the adjusted radius (a').

As described above, the plane strain fracture toughness ($J_{IC}$), which is a fracture toughness parameter, may be calculated from the adjusted load-depth curve through each method in the ductile fracture model and in the brittle fracture model, respectively.

In addition, the elastic-plastic stress intensity factor ($K_{JC}$) may be calculated by using the plane strain fracture toughness ($J_{IC}$).

The present method may further include an operation of calculating the plane strain fracture toughness ($J_{IC}$), and the plane strain fracture toughness ($J_{IC}$) may be calculated by the following Equation 1.

$$J_{IC} = J_e + J_p = \frac{(1-v^2)K_I^2}{E} + \eta_{pl}\frac{A_{pl}}{\pi(a')^2} \qquad [\text{Equation 1}]$$

Equation 1 is intended to calculate the plane strain fracture toughness ($J_{IC}$). Here, $J_e$ denotes the plane strain fracture toughness of the elastic deformation zone, and $J_p$ denotes the plane strain fracture toughness of the plastic zone. V refers to the Poisson's ratio of the specimen, and $K_I$ refers to the stress intensity factor. E denotes the elastic modulus of the specimen, and $\eta_{pl}$ denotes the distance factor according to the indenter. In addition, $A_{pl}$ refers to the area between the adjusted load-depth curve and the x-axis up to the crack initiation point (P) in FIG. 12, and a' refers to the adjusted radius of the indenter.

In addition, the stress intensity factor ($K_I$) may be calculated by using Equation 2 for the stress intensity factor ($K_I$) of the specimen, as follows.

$$K_I = \frac{9.8 \times L}{2a'\sqrt{\pi a'}} \quad \text{[Equation 2]}$$

Equation 2 is intended to calculate the stress intensity factor ($K_I$), wherein L denotes the load at the crack initiation point (P) in the adjusted load-depth curve.

In addition, the present invention may further include operation of calculating the elastic-plastic stress intensity factor ($K_{JC}$), which is one of the parameters, by using the plane strain fracture toughness ($J_{IC}$) through the following Equation.

$$K_{JC} = \sqrt{\frac{J_{IC} \cdot E}{(1-v^2)}} \quad \text{[Equation 3]}$$

Equation 3 is intended to calculate the elastic-plastic stress intensity factor ($K_{JC}$) that is one of the fracture toughness parameters to be used in the transition area in order to evaluate the ductile-brittle transition temperature.

The amount of impact energy that can be absorbed in the metal material varies with the temperature, and the ductile-brittle transition temperature refers to the temperature at which the amount of impact energy is abruptly changed.

When the elastic-plastic stress intensity factor ($K_{JC}$) obtained as described above is compared with the stress intensity factor that is measured in the actual fracture toughness testing, they match each other within an error range of 20%, which will be described in more detail with reference to FIG. 13.

FIG. 13 is a graph that compares the elastic-plastic stress intensity factor ($K_{JC}$) that is obtained by the actual standard testing with the elastic-plastic stress intensity factor ($K_{JC}$) that is obtained according to the present invention.

Referring to FIG. 13, the elastic-plastic stress intensity factor ($K_{JC}$) that is obtained according to the present invention is compared with the elastic-plastic stress intensity factor ($K_{JC}$) that is obtained by the actual standard testing.

At this time, in order to verify the model, the data was compared in relation to the materials, such as the structural steel, the stainless steel, or the pipe steels, which mainly require the fracture toughness evaluation. As a result of the comparison, it was confirmed that the data matched each other within an error range of 20%.

Furthermore, in the flat punch indentation testing, since the indentation behaviour exhibits the similarity to the tension/compression testing behaviour in the fully plastic zone, the yield strength and the strain hardening rate of the tensile properties may be evaluated based on the same.

In order to evaluate the yield strength and the strain hardening rate, the load-depth curve is converted into a stress-strain curve by using a representative stress-representative strain technique, and the yield strength and the strain hardening rate are evaluated by applying a standard tensile property measurement method. As a result of the evaluation, the data matched within an error range of 20%.

In the present invention, the fracture toughness, which is the fracture property of the specimen, is evaluated by using the plane strain fracture toughness ($J_{IC}$) and the elastic-plastic stress intensity factor in the flat punch indentation testing.

The plane strain fracture toughness ($J_{IC}$) and the elastic-plastic stress intensity factor ($K_{JC}$) are useful enough to be used for the evaluation of the physical properties in the field, such as the evaluation of a change in the fracture toughness depending on the temperature, the evaluation of DBTT (the ductile-brittle transition temperature), or the evaluation of the structural integrity, and they also show the resistance to the crack growth of the specimen.

As a result, referring to FIG. 14, a fracture toughness measuring method using the instrumented indentation testing may include operation S110 of executing the indentation testing up to a determined indentation depth (h) by using an indenter having a determined radius (a) in order to thereby create a determined load-depth curve.

In addition, after executing operation S120 of converting the determined load-depth curve into a normalized curve of the stress $$\left(\frac{L}{\pi a^2}\right)$$

and the indenter radius to the indentation depth (h/a), operation S130 of finding the crack initiation point (P) is executed by obtaining the crack initiation stress and the indenter radius-to-indentation depth at the crack initiation point (P) in the normalized curve.

Operation S140 of obtaining the adjusted radius (a') of the indenter is executed by calculating the crack initiation stress, the indenter radius-to-indentation depth at the crack initiation point (P), a configured radius of the indenter, or a configured indentation depth (h) of the indenter.

According to this, operation S150 of creating an adjusted load-depth curve is executed according to the indenter having the adjusted radius (a').

In addition, after executing calculating the plane strain fracture toughness ($J_{IC}$) by using the adjusted load-depth curve, operation of calculating the elastic-plastic stress intensity factor ($K_{JC}$) is executed by using the plane strain fracture toughness ($J_{IC}$).

The embodiments of the present invention give an effect of providing a fracture toughness measuring method using the instrumented indentation testing, which enables direct measurement of the physical properties in the field so that the structural integrity can be evaluated without separately collecting a specimen, and which enables the calculation of the fracture toughness by executing the indentation testing through a theoretical and practical approach in order to thereby identify the resistance to the crack growth in the specimen.

In addition, the embodiments of the present invention give an effect of providing a fracture toughness measuring method using the instrumented indentation testing, which is useful enough to be used for the evaluation of the physical properties in the field, such as the evaluation of a change in the fracture toughness depending on a temperature change or the evaluation of the structural integrity because the elastic-plastic stress intensity factor calculated according to the same matches the actually measured data within an error range of 20%.

Even if it was described above that all of the components of an embodiment of the present invention are coupled as a single unit or coupled to be operated as a single unit, the present invention is not necessarily limited to such an embodiment. That is, at least two elements of all structural elements may be selectively joined and operate without departing from the scope of the present invention.

Although a preferred embodiment of the present invention has been described for illustrative purposes, those skilled in the art will appreciate that various modifications, additions and substitutions are possible, without departing from the scope and spirit of the invention as disclosed in the accompanying claims. Therefore, the embodiments disclosed in the present invention are intended to illustrate the scope of the technical idea of the present invention, and the scope of the present invention is not limited by the embodiment. The scope of the present invention shall be construed on the basis of the accompanying claims in such a manner that all of the technical ideas included within the scope equivalent to the claims belong to the present invention.

What is claimed is:

1. A method for measuring a fracture toughness using an instrumented indentation testing of a fracture toughness measuring device, which measures a load and an indentation depth in real time while applying a load to a specimen by an indenter having a flat punch shape, the method comprising:

executing an indentation testing up to a determined indentation depth by the indenter having the flat punch shape and a determined radius to create a determined load-depth curve;

converting the determined load-depth curve into a normalized curve of a stress $$\left(\frac{L}{\pi a^2}\right)$$

and an indenter radius-to-indentation depth (h/a);

finding a crack initiation point (P) by calculating the indenter radius-to-indentation depth and a crack initiation stress at a time point (P) at which a crack begins in the normalized curve;

obtaining an adjusted radius of the indenter by calculating the crack initiation stress, the indenter radius-to-indentation depth at the crack initiation point (P), a configured radius of the indenter, or a configured indentation depth of the indenter; and creating an adjusted load-depth curve according to the indenter having the adjusted radius;

wherein the converting of the determined load-depth curve into the normalized curve comprises:

dividing the load (L) of the determined load-depth curve by a contact area ($\pi a^2$) between the indenter and the specimen; and dividing the indentation depth (h) by the radius (a) of the indenter to convert the determined load-depth curve into the normalized curve of the stress $$\left(\frac{L}{\pi a^2}\right)$$

and the indenter radius-to-indentation depth (h/a);

the method further comprising calculating the plane strain fracture toughness ($J_{IC}$) using the adjusted load-depth curve, wherein the plane strain fracture toughness ($J_{IC}$) is calculated by $$J_{IC} = J_e + J_p = \frac{(1-v^2)K_I^2}{E} + \eta_{pl}\frac{A_{pl}}{\pi(a')^2};$$

wherein $J_e$ denotes the plane strain fracture toughness of the elastic deformation zone, $J_p$ denotes the plane strain fracture toughness of the plastic zone, v refers to the Poisson's ratio of the specimen, $K_I$ refers to the stress intensity factor, E denotes the elastic modulus of the specimen, $\eta_{pl}$ denotes the distance factor according to the indenter, $A_{pl}$ refers to the area between the adjusted load-depth curve and the x-axis to the crack initiation point (P), and a' refers to the adjusted radius of the indenter; and calculating the elastic-plastic stress intensity factor ($K_{JC}$) by using the plane strain fracture toughness ($J_{IC}$), wherein the elastic-plastic stress intensity factor ($K_{JC}$) is calculated by $$K_{JC} = \sqrt{\frac{J_{IC} \cdot E}{(1-v^2)}}.$$

2. The method according to claim 1, wherein, when the specimen corresponds to a ductile fracture model, the finding of the crack initiation point (P) comprises obtaining the indenter radius-to-indentation depth of the crack initiation point (P) and the crack initiation stress at an intersection between a first line (L1), which extends from an elastic deformation zone of the normalized curve, and a second line (L2), which extends from a strain hardening zone thereof.

3. The method according to claim 2, wherein the obtaining of the adjusted radius of the indenter comprises calculating the adjusted radius of the indenter by configuring a point at which the indentation depth is 0.2 mm as the crack initiation point (P).

4. The method according to claim 1, wherein, when the specimen corresponds to a ductile fracture model, the finding of the crack initiation point (P) comprises obtaining the crack initiation stress and the indenter radius-to-indentation depth at the crack initiation point (P), using an offset method.

5. The method according to claim 4, wherein the obtaining of the adjusted radius of the indenter comprises calculating the adjusted radius of the indenter by configuring a point at which the indentation depth is 0.2 mm as the crack initiation point (P).

6. The method according to claim 1, wherein, when the specimen corresponds to a brittle fracture model, the finding of the crack initiation point (P) comprises obtaining the crack initiation stress and the indenter radius-to-indentation depth at the crack initiation point (P), using an offset method.

7. The method according to claim 6, wherein the obtaining of the adjusted radius of the indenter comprises calculating the adjusted radius of the indenter by configuring a thickness of the specimen to be 1 inch.

8. The method according to claim 1, wherein the stress intensity factor ($K_I$) is calculated by, $$K_I = \frac{9.8 \times L}{2a'\sqrt{\pi a'}}$$

wherein L denotes the load at the crack initiation point (P) in the adjusted load-depth curve.

* * * * *